United States Patent [19]

Georgiev et al.

[11] Patent Number: 4,769,468
[45] Date of Patent: Sep. 6, 1988

[54] 5-(ACYLOXYALKYL)-3-PHENYL-3-(1H-IMIDAZOL-1-YLMETHYL)-2-METHYLISOXAZOLIDINES

[75] Inventors: Vassil S. Georgiev, Rochester; George B. Mullen, Avon, both of N.Y.

[73] Assignee: Penwalt Corporation, Philadelphia, Pa.

[21] Appl. No.: 36,829

[22] Filed: Apr. 10, 1987

[51] Int. Cl.$^4$ .................. A01N 43/52; C07D 233/60
[52] U.S. Cl. .................................. 548/240; 548/341
[58] Field of Search ........................... 548/240

[56] References Cited

U.S. PATENT DOCUMENTS

| | | | |
|---|---|---|---|
| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1975 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | Georgiev | 548/240 |
| 4,723,021 | 2/1988 | Georgiev | 548/240 |

FOREIGN PATENT DOCUMENTS

| | | | |
|---|---|---|---|
| 171137 | 2/1986 | European Pat. Off. | 548/215 |
| 54-76579 | 6/1979 | Japan . | |

OTHER PUBLICATIONS

Sokolov, S. V. et al., Chemical Abstract 55:7399 (1961), Abstracting "Isoxazole Compounds III, Synthesis of Some Isoxazolylazoles", Zhur. Obshchei Khim. 30, pp. 1781–1787 (1960).
Kano, H. et al., Chem. Abstract 62:9139A (1965), Abstracting French 1,376,432 (Oct. 23, 1964).
Kano, H. et al., Chem. Abstract 63:8367a (1965), Abstracting French 1,380,177 (Nov. 27, 1964).
Takahi, Y. et al., Chem. Abstract 81:22233c (1974), Abstracting Japan Kokai 7,399,336 (Dec. 15, 1973).
Boyce, C. B. et al., Chem. Abstract 87:23258a (1977), Abstracting German Offen. 2,639,189 (Mar. 10, 1977).
Funaki, Y. et al., Chem. Abstract 92:128915u (1980), Abstracting Japan Kokai 79, 76,579 (Jun. 19, 1979).
Kelly, R. C. et al., Chem. Abstract 93:114498u (1980), Abstracting German Offen. 2,918,878 (Nov. 22, 1979).
Haken, P. T. et al., Chem. Abstract 93:132471j (1980), Abstracting Brit. Pat. Appln. 2,024,218 (Jan. 9, 1980).

*Primary Examiner*—Donald G. Daus
*Assistant Examiner*—Mark W. Noel

[57] ABSTRACT

Alkyl and aryl ester compounds, 5-(acyloxyalkyl)-3-phenyl-3-(1H-imidazol-1-ylmethyl)-2-methylisoxazolidines in which hydrogens of their phenyl rings may be replaced by halogen, lower alkyl, lower alkoxy or nitro groups are useful as antifungal agents.

6 Claims, No Drawings

5-(ACYLOXYALKYL)-3-PHENYL-3-(1H-IMIDAZOL-1-YLMETHYL)-2-METHYLISOXAZOLIDINES

BACKGROUND OF THE INVENTION

This invention relates generally to substituted 2-methylisoxazolidines and more particularly to 5-(acyloxyalkyl)-3-phenyl-3-(1H-imidazol-1-ylmethyl)-2-methylisoxazolidine esters which are useful as antifungal agents.

BRIEF SUMMARY OF THE INVENTION

In accordance with this invention there are provided compounds of the formula:

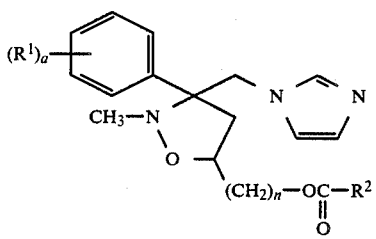

and the pharmaceutically acceptable acid addition salts thereof, in the form of their enantiomers or mixtures of their enantiomers including diastereoisomeric pairs of such enantiomers, wherein;

a = 1 or 2, $R^1$ is selected from hydrogen, lower alkyl, lower alkoxy, halogen, and combinations thereof, provided that the ortho position is hydrogen, $R^2$ is selected from lower alkyl, phenyl, and mono- or disubstituted phenyl where the substituents on the phenyl ring are selected from halogen, lower alkyl, lower alkoxy, nitro and combinations thereof, and the alkyl moiety $(CH_2)_n$ represents a branched or unbranched chain where n = 1 to 4.

DETAILED DESCRIPTION OF THE INVENTION

The ester compounds of this invention are useful as antifungal agents. They have in vitro activity against yeast and systemic mycoses and dermatophytes as determined by broth and agar testing techniques [McGinnis, M. R., *Laboratory Handbook of Medical Mycology*, Academic Press, N.Y., N.Y. (1980)]. The compounds prepared in Examples 1–5, below were found to have good to moderate inhibitory activity against a broad spectrum of organisms including trichophyton mentagrophytes, trichophyton rubrum, trichophyton tonsurans, and candida stellatoidea (minimum inhibitory concentration, MIC, of <0.7 to 70 ug/ml).

Because of the antifungal activity of the compounds of the invention they can be used, for example, in suitable liquid, semi-solid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

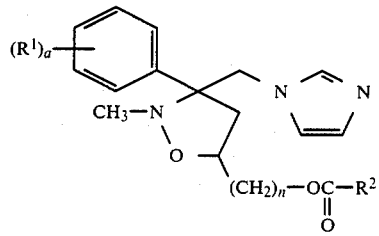

and the pharmaceutically acceptable acid addition salts thereof, in the form of their enantiomers or mixtures of their enantiomers including diastereoisomeric pairs of such enantiomers, wherein;

a = 1 or 2, $R_1$ is selected from hydrogen, lower alkyl, lower alkoxy, halogen, and combinations thereof, provided that the ortho position is hydrogen, $R_2$ is selected from lower alkyl, phenyl, and mono- or disubstituted phenyl where the substituents on the phenyl ring are selected from halogen, lower alkyl, lower alkoxy, nitro and combinations thereof, and the alkyl moiety $(CH_2)_n$ represents a branched or unbranched chain where n = 1 to 4.

By halogen is meant chlorine, bromine, fluorine and iodine with chlorine and fluorine being preferred. By lower alkyl is meant groups containing one to four (1–4) carbons and by lower alkoxy is meant groups containing one to six (1–6) carbons. In either case such groups with three or more carbons can have a branched or unbranched chain. Compounds having ortho substitution of the 3-phenyl group were not prepared probably due to steric hindrance.

The 5-(acyloxyalkyl)-3-phenyl-3-(1H-imidazol-1-ylmethyl)-2-methylisoxazolidines of the invention are obtained as mixtures of cis- and trans-diastereomers due to the presence in the isoxazolidine ring of two asymmetric carbon atoms. The diastereomeric mixture is conveniently separated by flash-chromatography on silica gel using halogenated hydrocarbons (preferably dichloromethane and chloroform), alkanols (preferably methanol and ethanol), ethyl acetate and such as eluents. The eluents may be utilized alone or in combinations such as the ones comprised of 95–99% by volume halogenated hydrocarbon and 1–5% by volume alkanol. The stereochemistry of the two asymmetric carbon atoms in the isoxazolidine ring may be determined by conventional methods that include X-ray crystallography, nuclear magnetic resonance spectroscopy, circular dichroism or optical rotatory dispersion. Both the cis and trans stereoisomers are resolvable into their optical enantiomers with (+) and (−) optical rotations by standard techniques such as fractional recrystallization of the diastereomeric salts with optically active organic acids such as (+) and (−)-tartaric acid, (+) and (−)-dibenzoyltartaric acid and the like.

The compounds of the invention can be synthesized starting with the reaction of an appropriate 2-imidazolylacetophenone precursor with N-methylhydroxylamine to furnish the corresponding nitrone derivative 1. The preparation of such nitrones is described in our copending application Ser. No. 900,856 filed Aug. 27, 1986 whose disclosure is incorporated herein by reference. Subsequent reaction of compound 1 with an appropriate 1-alkene alcohol 2 having three to six (3–6) carbons provides diastereomeric mixtures of cis and trans alkanol precursor 3. Reaction of the alkanol precursor with acetic anhydride or an appropriate acyl chloride provides the desired ester derivative 4, as a cis-/trans-diastereomeric mixture.

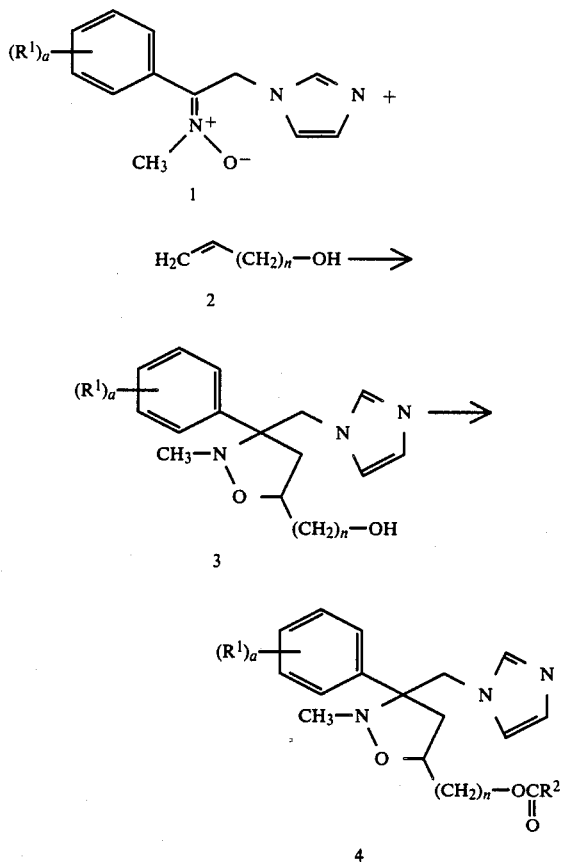

The compounds of the invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of the invention is further illustrated by the following examples.

EXAMPLE 1

5-(Acetyloxymethyl)-3-(4-chlorophenyl)-3-(1H-imidazol-1-ylmethyl)-2-methylisoxazolidine (4: $R^1=4$-Cl, $R^2=CH_3$, n=1)

Preparation of 5-(hydroxymethyl-3-(4-chlorophenyl)-3-(1H-imidazol-1-ylmethyl)-2-methylisoxazolidine precursor 3:

A solution of 24.97 g (100 mmol) of 1-(4-chlorophenyl)-2-(1H-imidazol-1-yl)-N-methylethanimine-N-oxide [prepared by reacting 2-(1H-imidazol-1-yl)-4'-chloroacetophenone (22.05 g, 0.10 mol), N-methylhydroxylamine hydrochloride (10.65 g, 0.127 mol), and sodium bicarbonate (10.84 g, 0.129 mol) in 300 ml of ethanol] and 14.0 ml (11.95 g, 200 mmol) of allyl alcohol (2, n=1) in 300 ml of toluene is refluxed for 19 hours under a nitrogen atmosphere. The reaction mixture is then cooled to room temperature and the solvent removed under reduced pressure. The residual oil is crystallized from isopropanol to provide 4.80 grams of the precursor 3.

Acetic anhydride (1.98 g, 0.0194 mol) is added to an ice-cold solution of 3.00 g (0.0097 mol) of 5-(hydroxymethyl)-3-(4-chlorophenyl)-3-(1H-imidazol-1-ylmethyl)-2-methylisoxazolidine (3: $R^1=4$-Cl, n=1) and 1.98 g (0.0194 mole) of triethylamine in 25 ml methylene chloride under a nitrogen atmosphere. The reaction is allowed to warm to room temperature, stirred for 18 hours, diluted to 100 ml with methylene chloride and extracted with saturated aqueous sodium bicarbonate (2×50 ml). The organic layer is dried over anhydrous magnesium sulfate and the solvent removed in vacuo, leaving a yellow oil which is crystallized from ethyl acetate, giving 2.01 g (59%) of compound 4 ($R^1=4$-Cl, $R^2=CH_3$, n=1), melting point 119°–121° C. (ethyl acetate). Anal. Calcd. for $C_{17}H_{20}ClN_3O_3$: C, 58.37; H, 5.76; N, 12.01; Cl, 10.13. Found: C, 58.26; H, 5.80; N, 11.90; Cl, 10.24.

EXAMPLE 2

5-Benzoyloxymethyl)-3-(4-chlorophenyl)-3-(1H-imidazol-1-ylmethyl)-2-methylisoxazolidine (4: $R^1=4$-Cl, $R^2=C_6H_5$, n=1)

Compound 4 ($R^1=4$-Cl, $R^2=C_6H_5$, n=1) is prepared by a method similar to that described in Example 1 by reacting 5-(hydroxymethyl)-3-(4-chlorophenyl)-3-(1H-imidazol-1-ylmethyl)-2-methylisoxazolidine (3: $R^1=4$-Cl, n=1) with benzoyl chloride. Flash-chromatography on neutral silica gel using a 98:2 by volume mixture of chloroform and methanol as eluent gives compound 4 ($R^1=4$-Cl, $R^2=C_6H_5$, n=1), melting point 95°–102° C. (ethyl acetate). Anal. Calcd. for $C_{22}H_{22}ClN_3O_3$: C, 64.15; H, 5.38; N, 10.20; Cl, 8.61. Found: C, 64.02; H, 5.48; N, 10.21; Cl, 8.88.

EXAMPLE 3

5-[(4-Chlorobenzoyl)oxymethyl]-3-(4-chlorophenyl)-3-(1H-imidazol-1-yl-methyl)-2-methylisoxazolidine Compound 4 ($R^1=4$-Cl, $R^2=C_6H_4Cl$-4, n=1) is prepared by a method similar to that described in Example 1 by reacting 5(hydroxymethyl)-3-(4-chlorophenyl)-3-(1H-imidazol-1-ylmethyl)-2-methylisoxazolidine (3: $R^1=4$-Cl, n=1) with 4-chlorobenzoyl chloride. Flash-chromatography on neutral silica gel using a 98:2 by volume mixture of chloroform and methanol as eluent gives compound 4 ($R^1=4$-Cl, $R^2=C_6H_4Cl$-4, n=1), melting point 122°–125° C. (ethyl acetate). Anal. Calcd. for $C_{22}H_{21}Cl_2N_3O_3$: C, 59.20; H, 4.74; N, 9.41; Cl, 15.89. Found: C, 59.06; H, 4.88; N, 9.32; Cl, 15.37.

EXAMPLE 4

5-[(4-Nitrobenzoyl)oxymethyl]-3-(4-chlorophenyl)-3-(1H-imidazol-1-ylmethyl)-2-methylisoxazolidine 4: $R^1=4$-Cl, $R^2=C_6H_4NO_2$-4, n=1)

Compound 4 ($R^1=4$-Cl, $R^2=C_6H_4NO_2$-4, n=1) is prepared by a method similar to that described in Example 1 by reacting 5-(hydroxymethyl)-3-(4-chlorophenyl)-3-(1H-imidazol-1-ylmethyl)-2-methylisoxazolidine (3: $R^1=4$-Cl, n=1) with 4-nitrobenzoyl chloride. Flash-chromatography on neutral silica gel using a 98:2 by volume mixture of chloroform and methanol as eluent gives compound 4 ($R^1=4$-Cl, $R^2=C_6H_4NO_2$-4, n=1), melting point 187°–190° C. (ethyl acetate). Anal. Calcd. for $C_{22}H_{21}ClN_4O_5$: C, 57.84; H, 4.63; N, 12.26; Cl, 7.76. Found: C, 57.75; H, 4.65; N, 12.21; Cl, 7.64.

EXAMPLE 5

5-(2-Acetyloxyethyl)-3-(4-chlorophenyl)-3-(1H-imidazol-1-ylmethyl)-2-methylisoxazolidine (4: $R^1=4$-Cl, $R^2=CH_3$, n=2)

Preparation of 5-(2-hydroxyethyl)-3-(4-chlorophenyl)-3-(1H-imidazol-1-ylmethyl)-2-methylisoxazolidine precursor 3:

A solution of 16.98 g (68 mmol) of 1-(4-chlorophenyl)-2-(1H-imidazol-1-yl)-N-methylethanimine N-oxide and 9.0 ml (7.49 g, 104 mmol) of 3-buten-1-ol in 150 ml of toluene is refluxed for 28 hours under a nitrogen atmosphere. The reaction mixture is then cooled to room temperature and the solvent removed under reduced pressure. The residual oil is crystallized from ethyl acetate to provide 4.01 g of precursor 3.

Compound 4 ($R^1=4$-Cl, $R^2=CH_3$, n=2) is prepared by a method similar to that described in Example 1 by reacting the 5-(2-hydroxyethyl)-3-(4-chlorophenyl)-3-(1H-imidazol-1-ylmethyl)-2-methylisoxazolidine (3: $R^1=4$-Cl, n=2) with acetic anhydride. Flash-chromatography on neutral silica gel using a 97:3 by volume mixture of chloroform and methanol as eluent gives compound 4 ($R^1=4$-Cl, $R^2=CH_3$, n=2), melting point 97°-98° C. (ether). Anal. Calcd. for $C_{18}H_{22}ClN_3O_3$: C, 59.42; H, 6.09; N, 11.55; Cl, 9.74. Found: C, 59.36; H, 6.14; N, 11.55; Cl 9.81.

The compounds of the present invention where $R^1$ includes mono- or disubstitution with halogen, lower alkyl and/or lower alkoxy are prepared starting with nitrones 1 formed from imidazolylacetophenones such as:

2-(1H-imidazol-1-yl)-4'-methylacetophenone, mp 133°-137° C., 2-(1H-imidazol-1-yl)-4'-methoxyacetophenone, mp 134°-137° C., 2-(1H-imidazol-1-yl)acetophenone, mp 117°-119° C., 2-(1H-imidazol-1-yl)-4'-fluoroacetophenone, mp 150°-155° C.

2-(1H-imidazol-1-yl)-3',4'-dichloroacetophenone, mp 124°-126° C., 2-(1H-imidazol-1-yl)-4'-chloro-3'-methylacetophenone, mp 116°-118° C., 2-(1H-imidazol-1-yl)-3'-methoxyacetophenone, mp 111°-113° C., and 2-(1H-imidazol-1-yl)-3'-methylacetophenone.

The compounds of the invention where $R^2$ includes substituted phenyl and where the substituents are lower alkyl and lower alkoxy are prepared according to the method of Example 2 by substituting for benzoyl chloride the aroyl chlorides, 4-methylbenzoyl chloride, bp 225° C.,
4-methoxybenzoyl chloride, mp 22° C.,
3-methylbenzoyl chloride bp 86° C./5 mm, and
3-methoxybenzoyl chloride, bp 123° C./5 mm.

The compounds of the invention where n=3 or 4 can be prepared according to the method of Example 1 by substituting for allyl alcohol to the alkenols, 4-penten-1-ol, bp 134°-137° C., and
5-hexen-1-ol, bp 78° C./25 mm.

Salts of the compounds of the invention can be prepared as known in the art, for example, by dissolving the compound in a 10:1 by volume mixture of ethanol and aqueous acid such as HCl or $HNO_3$, evaporating the solvent, and then recrystallizing the crude salt, for example, from methanol-ether, 1:3 by volume in the case of HCl salts, and ethanol in the case of $HNO_3$ salts.

We claim:

1. A compound of the formula:

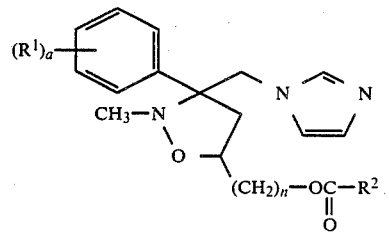

and the pharmaceutically acceptable acid addition salts thereof, in the form of their enantiomers or mixtures of their enantiomers including diastereoisomeric pairs of such enantiomers, wherein;

a=1 or 2, $R^1$ is selected from hydrogen, lower alkyl, lower alkoxy, halogen, and combinations thereof, provided that the ortho position is hydrogen, $R^2$ is selected from lower akyl, phenyl, and mono- or disubstituted phenyl where the substituents on the phenyl ring are selected from halogen, lower alkyl, lower alkoxy, nitro and combinations thereof, and the alkyl moiety $(CH_2)_n$ represents a chain where n=1 to 4.

2. The compound of claim 1 wherein the compound is 5-(acetyloxymethyl)-3-(4-chlorophenyl)-3-(1H-imidazol-1-ylmethyl)-2-methylisoxazolidine.

3. The compound of claim 1 wherein the compound is 5-(benzoyloxymethyl)-3-(4-chlorophenyl)-3-(1H-imidazol-1-ylmethyl)-2-methylisoxazolidine.

4. The compound of claim 1 wherein the compound is 5-[(4-chlorobenzoyl)oxymethyl]-3-(4-chlorophenyl)-3-(1H-imidazol-1-ylmethyl)-2-methylisoxazolidine.

5. The compound of claim 1 wherein the compound is 5-[(4-nitrobenzoyl)oxymethyl]-3-(4-chlorophenyl)-3-(1H-imidazol-1-ylmethyl)-2-methylisoxazolidine.

6. The compound of claim 1 wherein the compound is 5-(2-acetyloxyethyl)-3-(4-chlorophenyl)-3-(1H-imidazol-1-ylmethyl)-2-methylisoxazolidine.

* * * * *